United States Patent
Nieto Velasco et al.

(10) Patent No.: US 6,642,953 B1
(45) Date of Patent: Nov. 4, 2003

(54) SYSTEM FOR ANALYZING IMAGES PRODUCED BY BACTERIAL REACTIONS

(75) Inventors: Julio Nieto Velasco, Madrid (ES); Francisco Soria Melguizo, Madrid (ES); Gervasio Dopico Prieto, Madrid (ES)

(73) Assignee: Francisco Soria Melguizo, S.A., Madrid (ES)

( * ) Notice: Subject to any disclaimer, the term of this patent is extended or adjusted under 35 U.S.C. 154(b) by 0 days.

(21) Appl. No.: 09/554,512

(22) PCT Filed: Nov. 11, 1998

(86) PCT No.: PCT/ES98/00303

§ 371 (c)(1), (2), (4) Date: May 17, 2000

(87) PCT Pub. No.: WO99/28436

PCT Pub. Date: Jun. 10, 1999

(30) Foreign Application Priority Data

Dec. 2, 1997 (ES) .............................. 9702500

(51) Int. Cl.[7] .................................. H04N 7/18
(52) U.S. Cl. ..................... 348/61; 382/128; 435/287.3; 700/58
(58) Field of Search ........................... 348/61; 382/100, 382/128; 435/287.3; 700/58

(56) References Cited

U.S. PATENT DOCUMENTS 4,907,158 A * 3/1990 Kettler et al. ................. 700/58
5,290,701 A    3/1994 Wilkins .................... 435/287.3

FOREIGN PATENT DOCUMENTS

| EP | 0 193 385 | 9/1996 |
|----|-----------|--------|
| WO | 93/21511  | 10/1993 |
| WO | 95/16768  | 6/1995 |
| WO | 96/18721  | 6/1996 |

* cited by examiner

Primary Examiner—Chris Kelley
Assistant Examiner—Allen Wong
(74) Attorney, Agent, or Firm—Wenderoth, Lind & Ponack, L.L.P.

(57) ABSTRACT

It is based on an apparatus (1) forming a closed chamber (2) inside of which is installed an upper centered digital camera (15) oriented toward a removable support (17) over which is placed either a panel fitted with receptacles for holding the liquid culture mediums or a plate for placing on it a solid culture medium, the support (17) being located between lower lighting means (18) and upper lateral lighting means (19) complemented with light diffusers (20) and (21). The apparatus includes external operation indicators, switches, outlets and connections providing for appropriate operation and control through a central computer. The system captures and interprets the images produced by the reactions taking place in said culture mediums, either liquid or solid, allowing the bacterial reactions to be converted into values, in addition to analyzing microorganism growth.

14 Claims, 5 Drawing Sheets

SYSTEM FOR ANALYZING IMAGES PRODUCED BY BACTERIAL REACTIONS

OBJECT OF THE INVENTION

The invention refers to a system capable of converting bacterial reaction images into numerical values and analyzing microorganism growth by capturing images from a panel or plate.

The object of the invention consists in capturing and interpreting images produced by reactions taking place either in a liquid culture medium contained inside panel receptacles or on the surface of a solid culture medium in all-purpose laboratory receptacles, or so-called plates.

BACKGROUND OF THE INVENTION

Liquid culture mediums use support means commonly referred to as panels which are usually made of polystyrene, have a rectangular shape and are fitted with receptacles designed to contain various microbiological culture mediums, biochemical substrates and/or antimicrobial agents in liquid form in which metabolic reactions occur, the microbiological interpretation of which leads to the identification of a microorganism and/or the definition of its capacity to be neutralized by one or several antibiotics.

The cultures may also be performed with the use of another type of support or plates in the form of a container generally made of polystyrene, having various shapes and containing a single solid culture medium on which the bacterial reaction takes place.

Thus, traditionally, in the case of the panels, a visual inspection of the reactions occurring the various receptacles is performed in the laboratory, and, based on the panels' shape and color, the result probability is established according to general tables published for this purpose.

Automatic reading systems are presently used which, by measuring the optical density of the receptacles, assign a value interpreted as positive or negative by a computer program. Subsequently, another computer module establishes the result probability by combining the positive character of the partial reactions.

In the case of the plates, the approximation to the result has traditionally been more rudimentary in view of the smaller number of parameters involved, which are based mainly in the amount, size and color of the bacterial colonies.

The advantage of the these automatic systems—which measure optical densities—over the traditional visual inspection method lies in that it eliminates the user's subjectivity in interpreting reactions, since each reaction is translated into a numerical value.

However, these automatic systems present a serious problem and drawback in that they are unable to interpret both the morphological features and the growth patterns of the bacteria, which thus elude the result obtaining method of certain important elements, such as the form of bacterial growth, namely the base for obtaining microbiological results during the past decades.

DESCRIPTION OF THE INVENTION

The proposed system was conceived for the purpose of solving the above problems, allowing microbiological reactions to be converted to numerical values which are subsequently applied to a diagnosis software in order to establish the number of microorganisms present, revealing an infection, to identify the microorganisms present in the sample or to establish an organism's antimicrobial susceptibility pattern.

The following reactions are identified via the inventive system:

Bacterial colony size, color, shape and quantity.

Color development in biochemical substrate receptacles, indicative of the type of bacterial metabolism involved.

Development of compact shapes or turbidness in antibiotic receptacles that would reflect the microorganism's development capability in the presence of specific antimicrobial agent concentrations.

The formation of a circle around an antibiotic disc, or so-called "inhibiting halo".

The system is thus based on a device preferably having a prismatic-rectangular shape, the inside of which establishes a hermetically closed chamber of diverse shapes and dimensions provided they allow for appropriate focal distance between a digital camera lens and the panel or plate to be analyzed. The digital camera is internally mounted on an upper central support, an internal area near the logier end of the chamber being fitted with a support associated to an inlet/outlet feeder arranged for depositing the corresponding panels or plates, i.e. the objects to be analyzed in each case, characteristic in that the supports are interchangeable and may be of various types depending on the panels or plates to be processed.

The function of this support installed inside the chamber, as previously stated, is to allow the passage of light from the lower part of the object being processed or analyzed, and to center the object under the digital camera.

An internal lighting system is also provided, comprising four fluorescent tubes, two of which are installed along the sides and above the object to be processed and the other two are installed under the object to be processed, so that, depending on the type of image to be processed, the upper, lower or both fluorescent lights are activated, this being implemented either automatically, through the function management software, or manually, by means of a switch.

Externally, the chamber's front panel includes a series of function control LEDs and switches, in addition to the corresponding feeding mechanisms for inserting the panel or plate to be processed.

The chamber's rear panel includes external outlets leading to a central computer, to a TDM 436 card and a to digital camera and lighting system power supply line; however, depending on the assembly's operational requirements, other outlets may be installed or said outlets modified.

It must also be noted that the rear panel includes an access cover for internal cleaning, maintenance, component replacement, calibration, etc., purposes.

The system further includes a means of identifying the type of panel and the external data used for complementing the identification tests performed in the panel, and a means of establishing the position of each receptacle in the panel and calculating the panel area to be used for the reading.

According to the characteristics thus described, the system, in operation, must first perform a calibration of the camera by showing a camera histogram and its reading values on the screen of a control personal computer, so that, when an indicator lights up to signal the end of the calibration reading, a panel inserted in the internal support of the feeder may be read, said panel's upper surface being divided into three information areas, namely one corresponding to the type of panel identification area, another corresponding to the external information area and a third corresponding to the receptacles area.

Once the corresponding reading option is activated in the control software, the feeder is closed and an image reading instruction is issued enabling the system-generated data to be interpreted by the software, which assigns the analyzed bacteria a taxonomic classification and a code as to whether it is resistant or not to a given antibiotic or group of antibiotics.

DESCRIPTION OF THE DRAWINGS

In order to complement the description and help toward providing a better understanding of the characteristics of the invention according to a preferred practical embodiment thereof, a set of drawings is attached as an integral part of the description wherein the following is represented as illustrative and non-limiting in character.

Finally, FIG. 10 includes a graph corresponding to the calibration histogram.

PREFERRED EMBODIMENT OF THE INVENTION

Figures 1, 2:
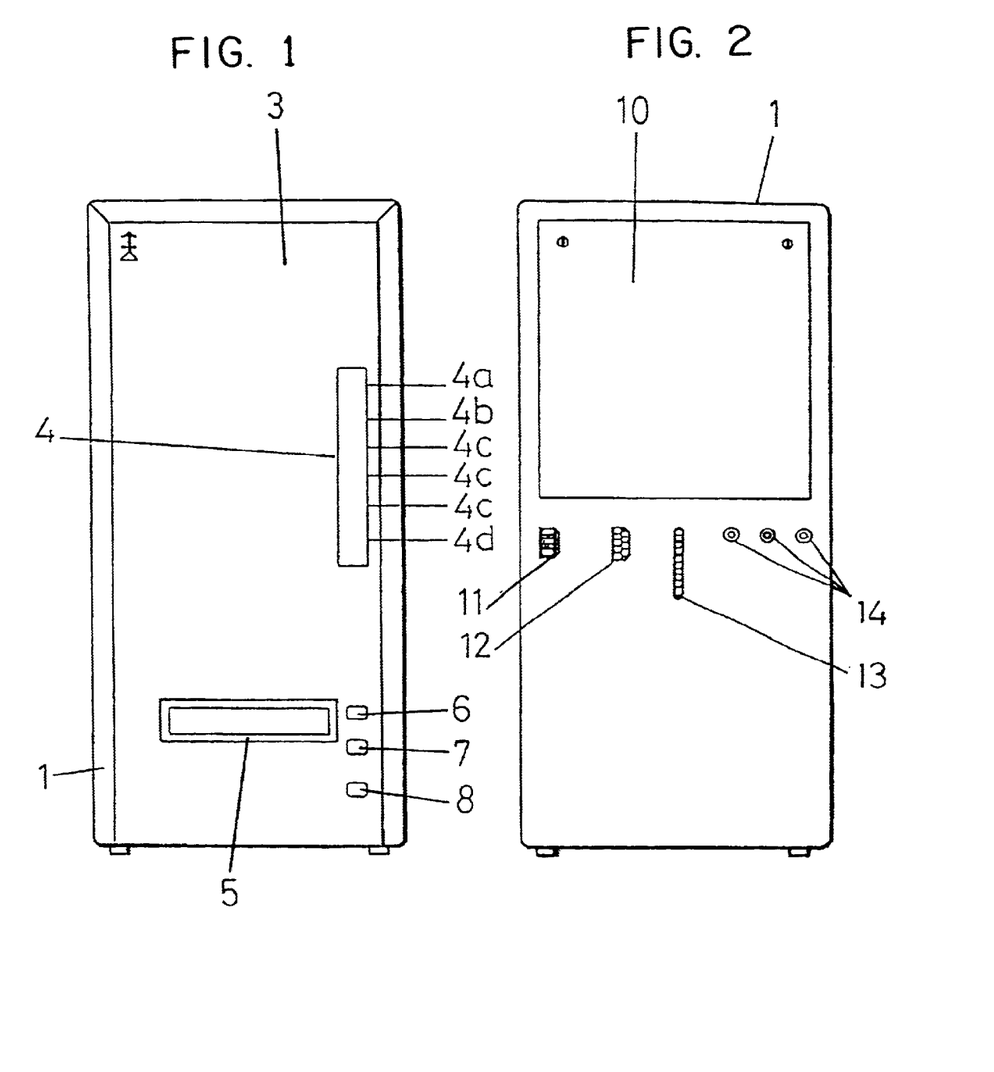
FIG. 1 shows an external front view of the apparatus or chamber which forms a part of the system that is the object of the invention.
FIG. 2 shows an external rear view of the same apparatus or chamber shown in the preceding figure.

In the light of the above figures, it is evident that the system of the invention is based on an apparatus fitted with a general housing (1) of a prismatic-rectangular shape which internally defines a closed chamber (2), characteristic in that its front panel (3) incorporates a series of external indicator LEDs (4) providing the following functions: indicator (4a) corresponds to the electric current inlet to in the chamber (2); indicator (4b) corresponds to the end of the calibration. The three next indicators (4c) correspond to 25% 50% and 75%, respectively, of the reading performed; indicator (4d) corresponds to the end of the reading.

Also, said front panel (3) includes a corresponding feeder (5), the function of which is described further on, an opening button (6) for the feeder, a contrast switch (7) and a general switch (8), in a manner that said indicators (4) and elements (5 to 8) constitute the means of controlling system functions and inserting the panel or plate to be read.

The rear panel (9) of apparatus (1) includes a cover (10) providing access to the internal components and an electric current outlet (11) for the auxiliary lighting systems; an electric current outlet (12) for the digital camera described hereunder; a communication port (13) for connection to the central computer; connections (14) to a TDM 436 module containing the calculating program for converting the image's calorimetric signals into numeric values, said connections (14) corresponding to blue, green and red colors which provide the signals corresponding to the percentages of said colors or calorimetric signals.

Figures 3, 4:
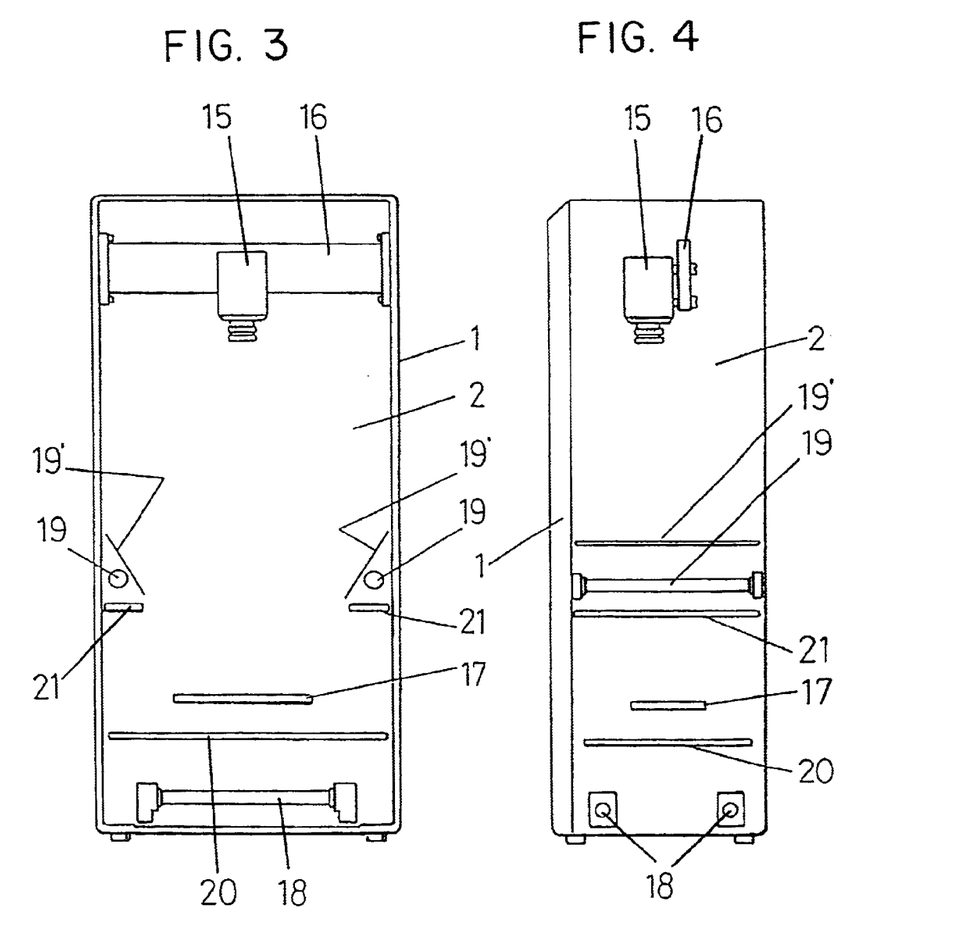
FIG. 3 shows a front view section through a vertical plane of the apparatus or chamber shown in the two preceding figures.
FIG. 4 shows an external side view, also in section through a vertical plane, of the same apparatus or chamber shown in the preceding figure.

Inside chamber (2) is fitted said digital camera (15), mounted on an upper support (16), the camera (15) being arranged in a central position and in line with the center of a support (17) on which the object to be analyzed is placed, namely the corresponding plate or panel. Support (17) is interchangeable and may vary in shape, depending on the feeder (5) and the type of panel or plate to be supported. In any case, said support (17) is part of the feeding device (5) itself, and constitutes the means allowing for the insertion of the supports to be processed, i.e. the panels and plates, since pressing the opening button (6) involves sliding the feeder (5) and thus the support (17) guided over rails and activated on its outward movement by any conventional system, from a simple pressure spring to a pneumatic mechanism or similar device.

Inside chamber (2), in addition to said digital camera (15) and support (17), are included lighting means in the form of a pair of fluorescent lamps (18) located on a lower position and a pair of fluorescent lamps (19) located at an intermediate lateral height, said fluorescent lights (18) and (19) being complemented with respective light diffusers (20) and (21), so that the former lie under the object to be processed, namely under the support (17), whereas the latter lie above it, characteristic in that the latter are complemented with a protective plate (19') forming an inclined metal screen preventing the radiations to interfere with the readings of the digital camera (15). The light diffusers (20) and (21) are preferably made of white crystal and are fitted for providing homogeneous light distribution, in the first case on the object to be processed and in the second case through the transparent polystyrene panel or plate receptacles.

Depending on the type of image to be processed, the upper fluorescent lights (19) or the lower fluorescent lights (18), or both simultaneously, are activated either automatically, through the software managing the various functions, or manually, through a contrast switch (7) located on the front panel (3).

Figure 6:
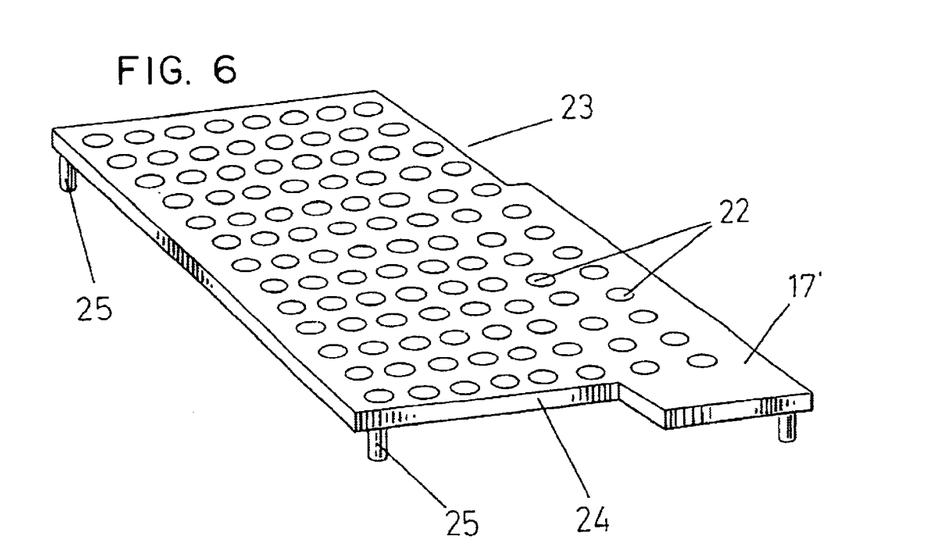
FIG. 6 shows a perspective view of a form of embodiment of a receptacle panel support.

FIG. 6 shows a support (17') for a receptacle panel, which support (17') is fitted with holes (22) for the panel's receptacles and recesses (23) and (24) for illuminating the panel's identification area and the external information area, said support (17') also including kingpins (25) for attachment to the corresponding feeder.

Figure 7:
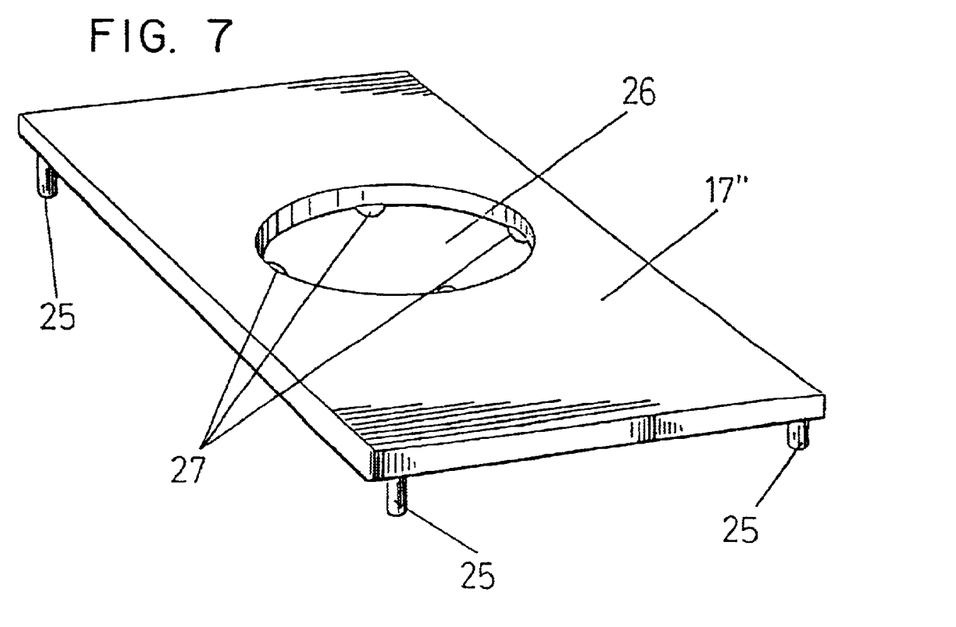
FIG. 7 shows a further perspective top view of a plate support.

FIG. 7 shows a plate support (17") fitted with kingpins for attachment to the feeder, in addition to a hole (26) for the lower lighting of the upper plate, and attachment flanges (27) for the plate itself.

Operation of the apparatus varies depending on whether the purpose is to analyze the image of a panel with its biochemical reactions and antimicrobial susceptibility patterns occurring in different sections of the same panel, or the image of a plate with a colony growth and/or inhibiting halos.

In any case, prior to the reading session corresponding to the same type of product, panel or plate, the apparatus must be calibrated after selecting the support (17) to be used, which in turn is dependent on the panel or plate to be processed.

Thus, once the support (17) is installed, which as previously stated must be shaped as shown in FIG. 6, reference (17'), or shaped as shown in FIG. 7, reference (17"), or otherwise shaped depending on the type of panel or plate, prior to inserting a panel or plate, in order to allow the light to pass freely through holes (22) or (26) through the support, the 'calibrate' option is executed from the control software residing in a personal computer and communicated with the apparatus through said communications port (13). The camera then shows the histogram and reading values on the control personal computer screen, as shown in the graph in FIG. 10, while indicator (4b) is activated to indicate the end of the calibration reading.

If the calibration is within stable ranges, the process comes to an end; otherwise, chamber (2) adjustments are necessary.

Figure 10:
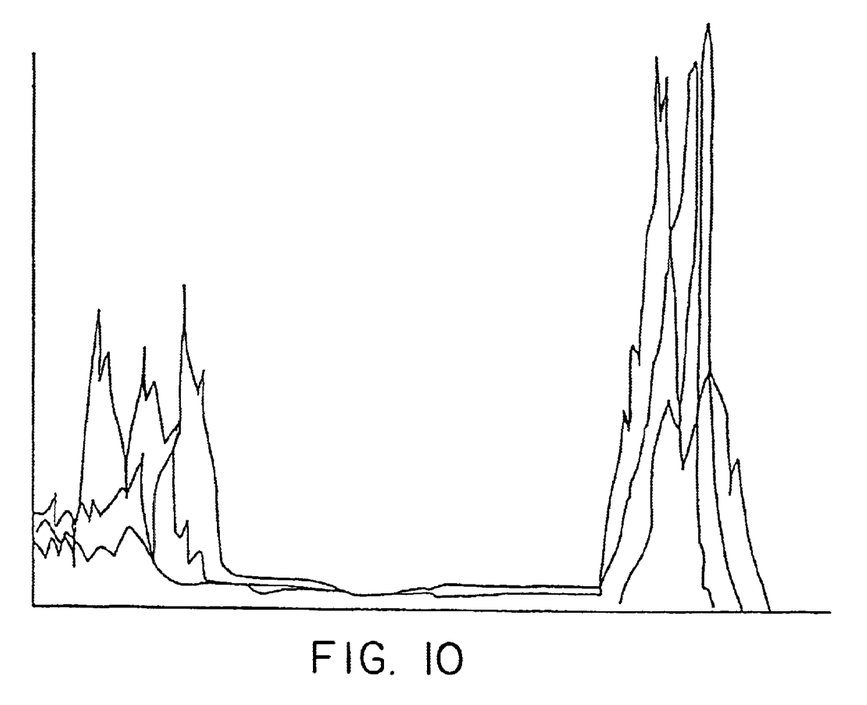

The histogram provided by the system, as shown in FIG. 10, must have its end peaks and valley as near as possible to the abscise axis.

Figure 5:
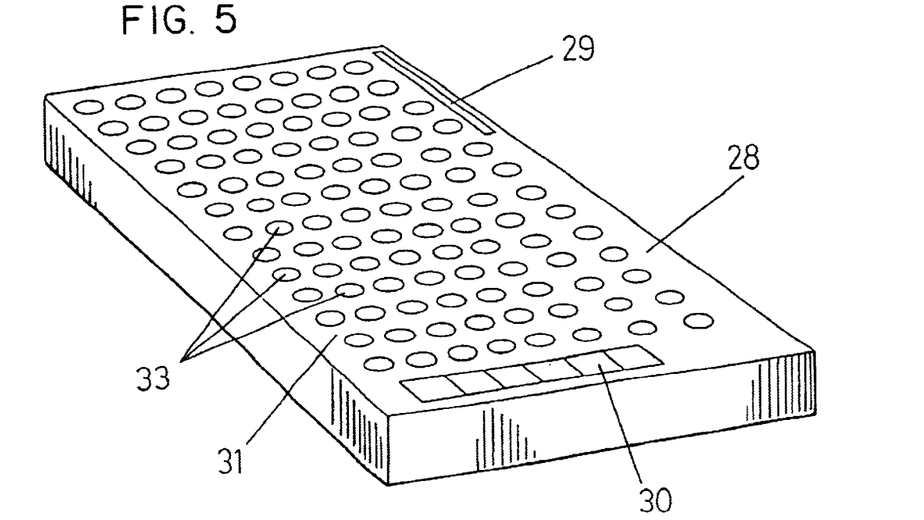
FIG. 5 shows a general top view o a panel with three identification sections corresponding to: type of panel, external information, and position of each receptacle.

The reading is performed as follows:

In the case of panels which, as previously stated, are polystyrene supports fitted with a number of receptacles containing biochemical substrates used for identifying a bacteria and others containing growth concentrations of antimicrobial agents used in establishing a bacteria's capacity to withstand the attack with the lowest possible antibiotic concentration—, the process starts by putting a reading algorithm to work which divides the panel's surface (28), shown in FIG. 5, into three sections corresponding to references (29), (30) and (31), with reference (29) corresponding to the type of panel identification area, reference (30) to the external information area and reference (31) to the receptacles area.

In the first case, and as previously stated, area (29) identifies the type of panel being used (three different types are available, according to microorganism, group of microorganisms or samples of microorganism sources). Area (29) is divided into four rectangles, although other geometrical shapes are acceptable, printed preferably in the upper left-hand section of panel (28) (for example, if the first and third receptacles in area (29) are full, this would identify an enterobacteria panel). Evidently, information on the type of panel is essential at the time of interpreting the response of the bacteria when faced with certain antibiotics.

Concerning area (30), foreseen for identifying external information used in complementing the identification tests included in the panel, the area comprises six squares, although other geometrical shapes are allowed, in which the user marks a point covering at least 90% of the surface if the bacteria in question have reacted positively to a specific laboratory technique (for example, a point covering the first square of the upper portion would indicate that the microorganism has reacted to the culture process at 18:00 hours as a result of an oxidase test).

Concerning the receptacles zone or area (31), this area establishes the position of each receptacle within the panel and calculates the panel's reading area, generating four values for each receptacle.

Figure 8:
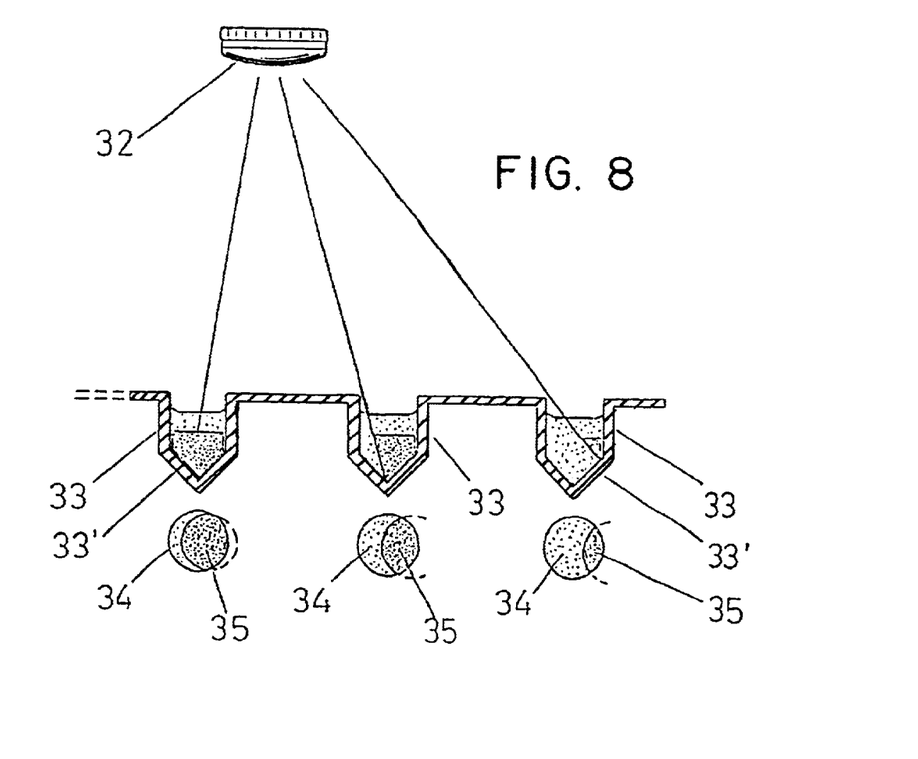
FIG. 8 shows a detail of the manner in which a selection of the reading area is performed according to the position of each receptacle in the corresponding panel.

As shown in FIG. 8, wherein reference (32) corresponds to the digital camera (15) focus, the receptacles (33) are cylindrical, the lower part or bottom (33') thereof being conical in shape; also, the selection of the area to be considered in respect to the vertical of the digital camera fixedly installed in the upper part of the apparatus is essential for detecting possible bacterial growth. In said figure, references (34) correspond to the liquid culture medium and references (35) to the bacterial growth detection area, which are different in each case depending on the location of the corresponding receptacle (33) in respect to the vertical of the digital camera (32) focus.

Out of the four values generated by the system in the course of processing a panel, the fist two are used for detecting bacterial metabolism calorimetric reactions, corresponding to color code and color saturation, whereas the third and fourth values are used for detecting bacterial growth, corresponding to the growth area, and the amount of light passing though each receptacle.

The values obtained for each receptacle (33) are then tabulated by the control software in order to identify the microorganism causing the infection and the best antibiotics against said infection, in their lower concentration.

Figure 9:
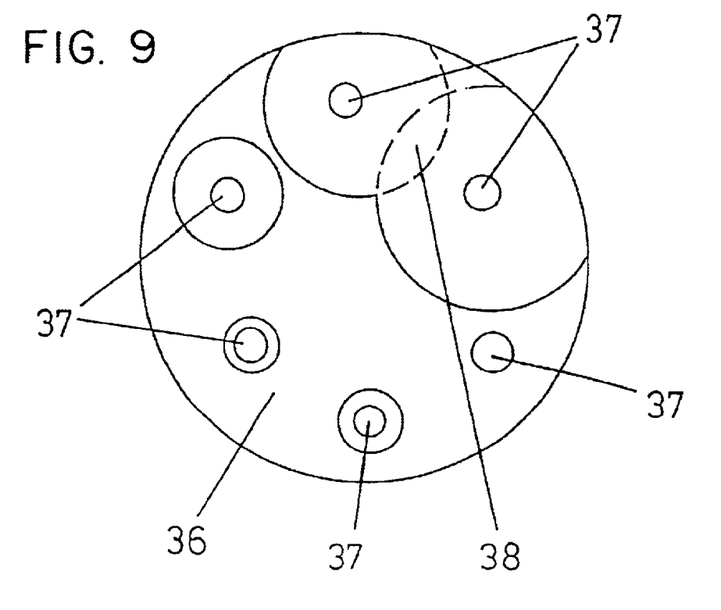
FIG. 9 shows a plan view of a plate including several discs impregnated by a selection of antibiotics.

FIG. 9 shows a plate (36) in he form of a circular polystyrene support, which may acquire different shapes and sizes, containing a solid culture medium on the surface of which is extended the microorganism suspension presumably causing the infection.

After inoculating the whole surface with the bacterial suspension, a selection of antibiotics-impregnated discs (37) is deposited thereon, the antibiotics contained in the discs then dissolving in and around the inoculated culture medium to achieve lower antibiotic concentrations in points further away from the edge of the disc. In said FIG. 9, the zone under reference (38) is the perimeter reconstruction zone resulting from the superposition of the 'inhibiting halos' from the two discs (37).

The capacity of the microorganisms to grow around an antibiotics disc, to a greater or lesser extent or none at all, determines their classification as sensitive or resistant to said antibiotic and thus establishes the antibiotic's usefulness as an agent for fighting against the infection.

The microorganism forms a circular zone around each disc, referred to above as an 'inhibiting halo', which is measured by the apparatus.

Thus, once the plate (36) is inserted in the chamber (2) and the order is issued to process the image, a reading algorithm is activated which divides the surface into as many sections as discs are deposited on the medium. It then verifies that no halos are superposed, which is a phenomenon resulting from two discs located near each other generating a halo of a diameter such that both overlap, so that, in the event of a superposition, the system reconstructs the most probable halo for each disc, namely the previously mentioned zone (38).

The average diameter of each inhibiting halo is then calculated on the basis of direct measurement of the diameters as such, or some other parameter leading to this information. Three measurements are performed on each halo in order to calculate the average diameter, although a different number of measurements could likewise be implemented.

On completing the measurements, the system associates each measurement to a disc (37), according to its location on the plate (36), starting from the one on the upper portion and advancing clockwise.

The values obtained for each disc (37) are then tabulated by the control software in order to determine the antibiotics that are most convenient for fighting against the microorganism causing the infection.

Obviously, in addition to the panel and plate readings according to the previous description, a colony recount must be conducted, this naturally consisting in counting the number of bacterial groups that have managed to grow on the surface of a solid medium; according to the object of the invention, said colony recount starts with a technique consisting in "sowing" a bacterial suspension on the surface of a medium contained on a plate, incubating it at 37° C. and establishing the number of groups (colonies) appearing after an 18- to 14-hour incubation period.

The system and the means associated thereto perform a color assessment of the base medium on which the suspension was inoculated, the numeric values ranging from 0 to 256.

In this respect, a colony is considered to be the smallest number of adjacent pixels showing a 20% difference in color above or below the base medium value.

Once the surface of a colony is established, said surface is extrapolated to all the areas presenting a 20% difference and a calculation is made as to how many times the surface of a colony is contained in the overall surface; the value obtained is then tabulated, this operation being performed by the control software associated to the system in order to decide whether or not the number of colonies is indicative of the presence of an infectious process.

What is claimed is:

1. A system for analyzing images produced by bacterial reactions, allowing microbiological reactions to be converted into numerical values which are subsequently used by a diagnosis software to determine: the amount of microorganisms present, indicative of an infection; the identification of the microorganism present in the sample; and the infection-causing organism's antimicrobial susceptibility pattern; wherein the reactions produced by the images which are to be captured and interpreted by means of the system proper occur in liquid culture mediums contained inside panel receptacles or on the surface of a solid culture medium or so-called plate, characteristic in that it comprises an apparatus (1) having a preferably prismatic-rectangular shape which internally defines a closed hermetic chamber (2) internally fitted with a digital camera (15) mounted on a support (16), a removable support (17) for the panel or plate concerned, and lighting means (18) and (19) complemented with light diffusers (20) and (21), whereas externally the apparatus (1), in correspondence with its front panel (3), includes a series of luminous indicators (4), a feeder (5) associated to the corresponding removable support (17), an opening button (6) acting on the feeder (5), a contrast switch (7) and a general switch (8); the rear panel (9) of said apparatus (1) being designed to include a cover (10) providing access to the internal components, as well as outlets (11), (12) and (13) supplying current to the lighting fixture and to the chamber, and a port for communicating with the central computer, respectively, said rear panel (9) also including the connections (14) to a TDM 436 control module.

2. A system for analyzing images produced by bacterial reactions, according to claim 1, characteristic in that the support (17) is mounted in a coupling/uncoupling relationship with the feeder (5), the latter being guided in its inward and outward movements to allow for the corresponding receptacle panel (28) or plate (36) to be inserted.

3. A system for analyzing images produced by bacterial reactions, according to claim 1, characteristic in that the support (17') for the receptacle panels (28) is shaped according to the shape of the panels, said support being fitted with specific lateral recesses (23) and (24) and with kingpins (25) for attachment to the feeder (5), and also holes (22) for the receptacles (33) of the corresponding panel (18).

4. A system for analyzing images produced by bacterial reactions, according to claim 1, characteristic in that the support (17") for the plate (36) is fitted with kingpins (25) for attachment to the feeder (5) and a hole (26) for the disc that constitutes the plate (36), in addition to flanges (27) for attaching the plate.

5. A system for analyzing images produced by bacterial reactions, according to claim 1, characteristic in that, on the upper surface of panel (28), three areas (29), (30) and (31) are established, the first one for identifying the type of panel, the second for identifying the external information and the third for identifying the receptacle, with areas (29) and (30) corresponding to recesses (23) and (24) in the support (17).

6. A system for analyzing images produced by bacterial reactions, according to claim 1, characteristic in that the support (17) fitted inside the chamber (2) of apparatus (1) is located above the lighting means which constitute the fluorescent lights (18) and below the lighting means which constitute the fluorescent lights (19), the former being installed in the lower portion, whereas the lighting means or fluorescent light tubes (19) are located along the sides at an intermediate height, both being complemented by light diffusers (20) and (21), while the fluorescent light tubes (19) are complemented with metal plates (19') which interrupt the trajectory of the light beam between the upper digital camera (15) and the panel over support (17).

7. A system for analyzing images produced by bacterial reaction, according to claim 2, characteristic in that the support (17') for the receptacle panels (28) is shaped according to the shape of the panels, said support being fitted with specific lateral recesses (23) and (24) and with kingpins (25) for attachment to the feeder (5), and also holes (22) for the receptacles (33) of the corresponding panel (18).

8. A system for analyzing images produced by bacterial reactions, according to claim 2, characteristic in that the support (17") for the plate (36) is fitted with kingpins (25) for attachment to the feeder (5) and a hole (26) for the disc that constitutes the plate (36), in addition to flanges (27) for attaching the plate.

9. A system for analyzing images produced by bacterial reactions, according to claim 2, characteristic in that, on the upper surface of panel (28), three areas (29), (30) and (31) are established, the first one for identifying the type of panel, the second for identifying the external information and the third for identifying the receptacle, with areas (29) and (30) corresponding to recesses (23) and (24) in the support (17).

10. A system for analyzing images produced by bacterial reactions, according to claim 3, characteristic in that, on the upper surface of panel (28), three areas (29), (30) and (31) are established, the first one for identifying the type of panel, the second for identifying the external information and the third for identifying the receptacle, with areas (29) and (30) corresponding to recesses (23) and (24) in the support (17).

11. A system for analyzing images produced by bacterial reactions, according to claim 2, characteristic in that the support (17) fitted inside the chamber (2) of apparatus (1) is located above the lighting means which constitute the fluorescent lights (18) and below the lighting means which constitute the fluorescent lights (19), the former being installed in the lower portion, whereas the lighting means or fluorescent light tubes (19) are located along the sides at an intermediate height, both being complemented by light diffusers (20) and (21), while the fluorescent light tubes (19) are complemented with metal plates (19') which interrupt the trajectory of the light beam between the upper digital camera (15) and the panel over support (17).

12. A system for analyzing images produced by bacterial reactions, according to claim 3, characteristic in that the support (17) fitted inside the chamber (2) of apparatus (1) is located above the lighting means which constitute the fluorescent lights (18) and below the lighting means which constitute the fluorescent lights (19), the former being installed in the lower portion, whereas the lighting means or fluorescent light tubes (19) are located along the sides at an intermediate height, both being complemented by light diffusers (20) and (21), while the fluorescent light tubes (19) are complemented with metal plates (19') which interrupt the trajectory of the light beam between the upper digital camera (15) and the panel over support (17).

13. A system for analyzing images produced by bacterial reactions, according to claim 4, characteristic in that the support (17) fitted inside the chamber (2) of apparatus (1) is located above the lighting means which constitute the fluorescent lights (18) and below the lighting means which constitute the fluorescent lights (19), the former being installed in the lower portion, whereas the lighting means or fluorescent light tubes (19) are located along the sides at an intermediate height, both being complemented by light diffusers (20) and (21), while the fluorescent light tubes (19) are complemented with metal plates (19') which interrupt the trajectory of the light beam between the upper digital camera (15) and the panel over support (17).

14. A system for analyzing images produced by bacterial reactions, according to claim 5, characteristic in that the support (17) fitted inside the chamber (2) of apparatus (1) is located above the lighting means which constitute the fluorescent lights (18) and below the lighting means which constitute the fluorescent lights (19), the former being installed in the lower portion, whereas the lighting means or fluorescent light tubes (19) are located along the sides at an intermediate height, both being complemented by light diffusers (20) and (21), while the fluorescent light tubes (19) are complemented with metal plates (19') which interrupt the trajectory of the light beam between the upper digital camera (15) and the panel over support (17).

* * * * *